United States Patent
Zhang

(10) Patent No.: US 9,050,014 B2
(45) Date of Patent: Jun. 9, 2015

(54) SYSTEM FOR CARDIAC ARRHYTHMIA DETECTION AND CHARACTERIZATION

(71) Applicant: Siemens Medical Solutions USA, Inc., Malvern, PA (US)

(72) Inventor: Hongxuan Zhang, Palatine, IL (US)

(73) Assignee: Siemens Medical Solutions USA, Inc., Malvern, PA (US)

(*) Notice: Subject to any disclaimer, the term of this patent is extended or adjusted under 35 U.S.C. 154(b) by 204 days.

(21) Appl. No.: 13/626,930

(22) Filed: Sep. 26, 2012

(65) Prior Publication Data

US 2013/0158422 A1 Jun. 20, 2013

Related U.S. Application Data

(60) Provisional application No. 61/570,321, filed on Dec. 14, 2011.

(51) Int. Cl.
| A61B 5/0468 | (2006.01) |
| A61B 5/0464 | (2006.01) |
| A61B 5/0452 | (2006.01) |
| A61B 5/044  | (2006.01) |

(52) U.S. Cl.
CPC .............. *A61B 5/0468* (2013.01); *A61B 5/0452* (2013.01); *A61B 5/044* (2013.01); *A61B 5/0464* (2013.01)

(58) Field of Classification Search
CPC .... A61B 5/044; A61B 5/0468; A61B 5/0464; A61B 5/0452
USPC ................................................ 600/516, 521
See application file for complete search history.

(56) References Cited

U.S. PATENT DOCUMENTS

| 4,974,162 A | 11/1990 | Siegel et al. |
| 5,054,496 A | 10/1991 | Wen et al. |
| 5,199,438 A | 4/1993 | Pearlman |
| 5,211,179 A | 5/1993 | Haberl et al. |
| 5,411,031 A * | 5/1995 | Yomtov ......................... 600/519 |
| 5,513,644 A | 5/1996 | McClure et al. |
| 5,609,158 A | 3/1997 | Chan |
| 5,682,900 A | 11/1997 | Arand et al. |

(Continued)

OTHER PUBLICATIONS

Stuart E. Sheifer, MD, et al., "Unrecognized Myocardial Infarction", Annals of Internal Medicine, Nov. 6, 2001, vol. 135, Issue 9, pp. 801-811.

(Continued)

*Primary Examiner* — Niketa Patel
*Assistant Examiner* — William Levicky

(57) ABSTRACT

A system for analyzing cardiac electrophysiological signals includes an acquisition processor for acquiring signal data representing heart electrical activity over multiple heart cycles. An individual heart cycle comprises a signal portion between successive sequential R waves. A time interval detector uses a signal peak detector for detecting multiple successive time intervals including individual time intervals comprising a time interval between a first peak occurring in a first heart cycle and a second peak occurring in at least one of, (a) a successive sequential second heart cycle and (b) a third heart cycle successive and sequential to the second heart cycle. A data processor processes the multiple detected successive time intervals by, determining at least one interval parameter of, a mean, variance and standard deviation of the time intervals and generating an alert message in response to the interval parameter.

18 Claims, 10 Drawing Sheets

(56) References Cited

U.S. PATENT DOCUMENTS

| | | | |
|---|---|---|---|
| 5,817,027 A | 10/1998 | Arand et al. | |
| 5,846,263 A | 12/1998 | Peterson et al. | |
| 6,192,273 B1 | 2/2001 | Igel et al. | |
| 6,421,554 B1* | 7/2002 | Lee et al. | 600/509 |
| 6,577,894 B2* | 6/2003 | Callahan et al. | 600/516 |
| 6,589,188 B1* | 7/2003 | Street et al. | 600/538 |
| 6,615,083 B2* | 9/2003 | Kupper | 607/25 |
| 6,622,042 B1 | 9/2003 | Thacker | |
| 6,773,397 B2 | 8/2004 | Kelly | |
| 6,904,314 B1* | 6/2005 | Brewer et al. | 607/7 |
| 7,123,954 B2 | 10/2006 | Narayan et al. | |
| 7,225,015 B1 | 5/2007 | Min et al. | |
| 7,269,454 B2 | 9/2007 | Sherman | |
| 7,474,916 B2 | 1/2009 | Gutierrez | |
| 7,542,800 B2 | 6/2009 | Libbus et al. | |
| 7,727,157 B2* | 6/2010 | Sharrock | 600/495 |
| 7,764,997 B2 | 7/2010 | Chen et al. | |
| 2004/0243192 A1* | 12/2004 | Hepp et al. | 607/17 |
| 2006/0025824 A1* | 2/2006 | Freeman et al. | 607/5 |
| 2008/0097537 A1* | 4/2008 | Duann et al. | 607/14 |
| 2009/0275849 A1* | 11/2009 | Stewart | 600/518 |
| 2009/0281441 A1* | 11/2009 | Zhang et al. | 600/516 |
| 2011/0098766 A1* | 4/2011 | Gunderson | 607/14 |

OTHER PUBLICATIONS

S. Abboud, et al., "Detection of transient myocardial ischemia by computer analysis of standard and signal-averaged high-frequency electrocardiograms in patents undergoing percutaneous transluminal coronary angioplasty", Circulation, vol. 76, 585-596.

Hamilton, Patrick S., et al., "Quantitative Investigation of QRS Detection Rules Using the MIt/BIH Arrhythmia Database", IEEE Translations on Biomedical Engineering, issue date Dec. 1986, vol. BME-33, issue 12, pp. 1157-1165.

Huiskamp, G., Van Oosterom, A., "The depolarization sequence of the human heart surface computed from measured body surface potentials", IEEE Transactions on Biomedical Engineering, vol. 35, issue 12, publication year 1998, pp. 1047-1058.

Greensite, F. Huiskamp G., "An improved method for estimating epicardial potentials from the body surface", IEEE Transactions on Biomedical Engineering, vol. 45, issue 1, publication year 1998, pp. 98-104.

Huiskamp G., "Simulation of depolarization in a membrane equations-based model of the anisotropic ventricle", IEEE Transactions on Biomedical Engineering, vol. 45, issue 7, publication year 1998, pp. 847-855.

Laguana, P., et al., "Low-pass differentiators for biological signals with known spectra: application to ECG signal processing", IEEE Transactions on Biomedical Engineering, vol. 37, issue 4, publication year 1990, pp. 420-425.

Olivier Meste, et al., "Ventricular late potentials characterization in time-frequency domain by means of a wavelet transform", IEEE Transactions on Biomedical engineering, vol. 41, No. 7, Jul. 1994, p. 625.

* cited by examiner

FIGURE 3

| defined parameter | calculation and derived parameter (average value, variance, standard deviation, parameter dispersity, parameter variation) | Electrophysiological functions |
|---|---|---|
| PP synchronization time | $mean(T_{PP})$<br>$Var(T_{PP})$<br>$STD(T_{PP})$<br>$MAX(T_{PP})/STD(T_{PP})$<br>$mean(T_{PP})/Var(T_{PP})$ | These PP synchronization timing parameter and calculation parameters describe the atrial depolarization interval changes and variation range which facilitate atrial function mapping and diagnosis |
| QQ synchronization time | $mean(T_{QQ})$<br>$Var(T_{QQ})$<br>$STD(T_{QQ})$<br>$MAX(T_{QQ})/STD(T_{QQ})$<br>$mean(T_{QQ})/Var(T_{QQ})$ | These QQ synchronization timing parameter and calculation parameters describe the ventricular electrophysiological onset timing changes and variation range which facilitate atrial to ventricular transition function mapping and diagnosis |
| RR synchronization time | $mean(T_{RR})$<br>$Var(T_{RR})$<br>$STD(T_{RR})$<br>$MAX(T_{RR})/STD(T_{RR})$<br>$mean(T_{RR})/Var(T_{RR})$ | These RR synchronization timing parameter and calculation parameters describe the ventricular depolarization interval changes and variation range which facilitate ventricular function mapping and diagnosis |
| SS synchronization time | $mean(T_{SS})$<br>$Var(T_{SS})$<br>$STD(T_{SS})$<br>$MAX(T_{SS})/STD(T_{SS})$<br>$mean(T_{SS})/Var(T_{SS})$ | These SS synchronization timing parameter and calculation parameters describe the end timing changes of ventricular depolarization and variation range which facilitate ventricular function mapping and diagnosis |
| TT synchronization time | $mean(T_{TT})$ | These TT synchronization timing parameter and |

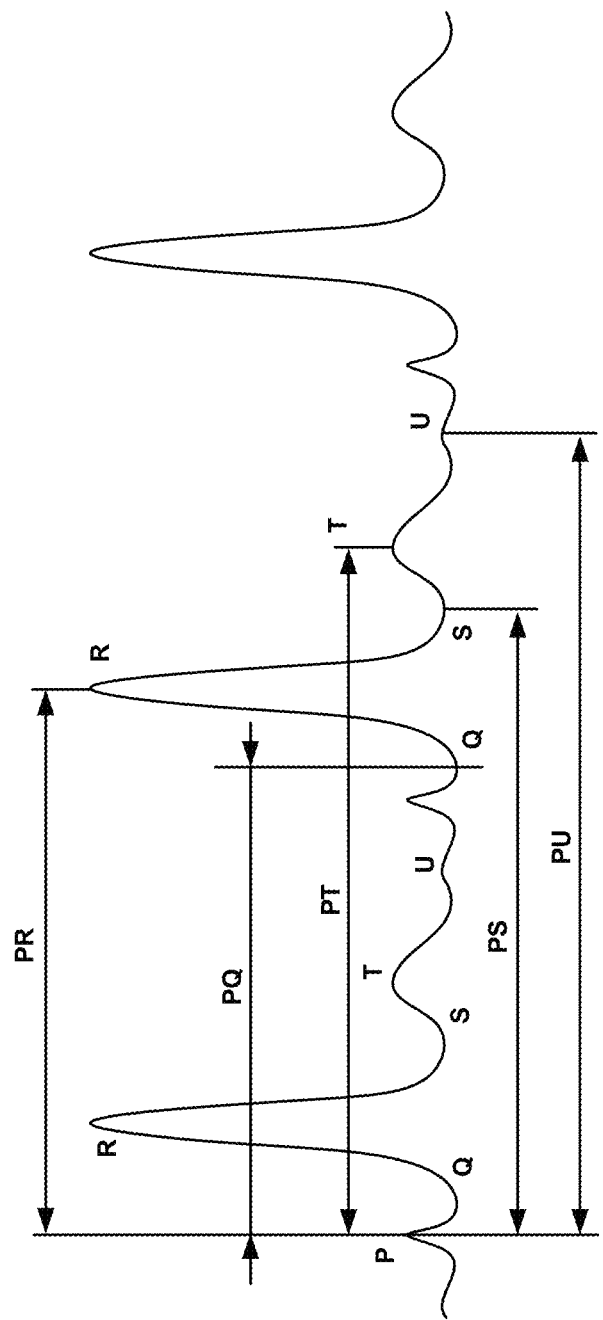

SYSTEM FOR CARDIAC ARRHYTHMIA DETECTION AND CHARACTERIZATION

This is a non-provisional application of provisional application Ser. No. 61/570,321 filed Dec. 14, 2011, by H. Zhang.

FIELD OF THE INVENTION

This invention concerns a system for analyzing cardiac electrophysiological signals by analyzing detected successive time intervals between peaks in successive heart cycles.

BACKGROUND OF THE INVENTION

Early cardiac arrhythmia detection and characterization, such as of atrial fibrillation, myocardial ischemia/infarction, and ventricle tachycardia, is desirable for rhythm management of cardiac disorders and irregularities. However, known systems typically fail to detect and provide a quantitative visualization of small ECG signal morphology and latency changes. In addition, known systems for cardiac arrhythmia identification and analysis based on ECG signals are subjective and need extensive expertise and clinical experience for accurate interpretation and appropriate cardiac rhythm management.

A 12-lead electrocardiogram (ECG) and multi-channel intra-cardiac electrogram (ICEG) are diagnostic reference standards used for evaluating cardiac rhythm and events and detecting Coronary Artery Disease (CAD). Cardiac arrhythmia analysis including of atrial fibrillation (AF), myocardial ischemia (MI), ventricular tachycardia/fibrillation (VT/VF), is used, for the management of cardiac disorders. Analysis involves ECG signal waveform and associated time domain parameter examination for cardiac arrhythmia detection and characterization involving P wave, QRS complex, ST segment and T wave analysis. However, known waveform and parameter analysis is often subjective and time-consuming, and requires extensive expertise and clinical experience for accurate interpretation and proper cardiac rhythm management. Known analysis systems typically fail to localize occurrence time and trend of cardiac events, such as of occurrence of arrhythmia.

Early cardiac atrial arrhythmia and pathology recognition is desirable for rhythm management of cardiac disorders and irregularities. Known waveform morphology and time domain parameter analysis typically focuses on electrophysiological wave changes which may fail to provide early detection and characterization of cardiac function pathologies which are usually small in an early stage. Known cardiac arrhythmia analysis is typically based on time domain parameters (such as signal amplitude, time intervals) including parameters of an electrophysiological signal from a single chamber associated with a P wave for atrial fibrillation and a QRS wave for ventricular arrhythmias. Known cardiac arrhythmia (such as fibrillation) analysis methods lack reliability, especially in a noisy environment since atrial activities may be buried in noise and artifacts. A system according to invention principles addresses these deficiencies and related problems.

SUMMARY OF THE INVENTION

A system analyzes and characterizes cardiac electrophysiological signals (including surface ECG signals and intra-cardiac electrograms) to identify pathology related distortion based on different types of information including timing, frequency, electrophysiological activity information acquired by synchronization and visualization. A system for analyzing cardiac electrophysiological signals includes an acquisition processor for acquiring signal data representing heart electrical activity over multiple heart cycles. An individual heart cycle comprises a signal portion between successive sequential R waves. A time interval detector uses a signal peak detector for detecting multiple successive time intervals including individual time intervals comprising a time interval between a first peak occurring in a first heart cycle and a second peak occurring in at least one of, (a) a successive sequential second heart cycle and (b) a third heart cycle successive and sequential to the second heart cycle. A data processor processes the multiple detected successive time intervals by, determining at least one interval parameter of, a mean, variance and standard deviation of the time intervals and generating an alert message in response to the interval parameter.

BRIEF DESCRIPTION OF THE DRAWING

FIG. 3 shows a Table identifying statistical parameters derived from defined time intervals and associated electrophysiological functions, according to invention principles.

FIG. 4 shows time intervals between a first peak of a first ECG wave type occurring in a first heart cycle and a second peak of a different second ECG wave type occurring in a successive sequential different heart cycle, according to invention principles.

DETAILED DESCRIPTION OF THE INVENTION

Figure 1:
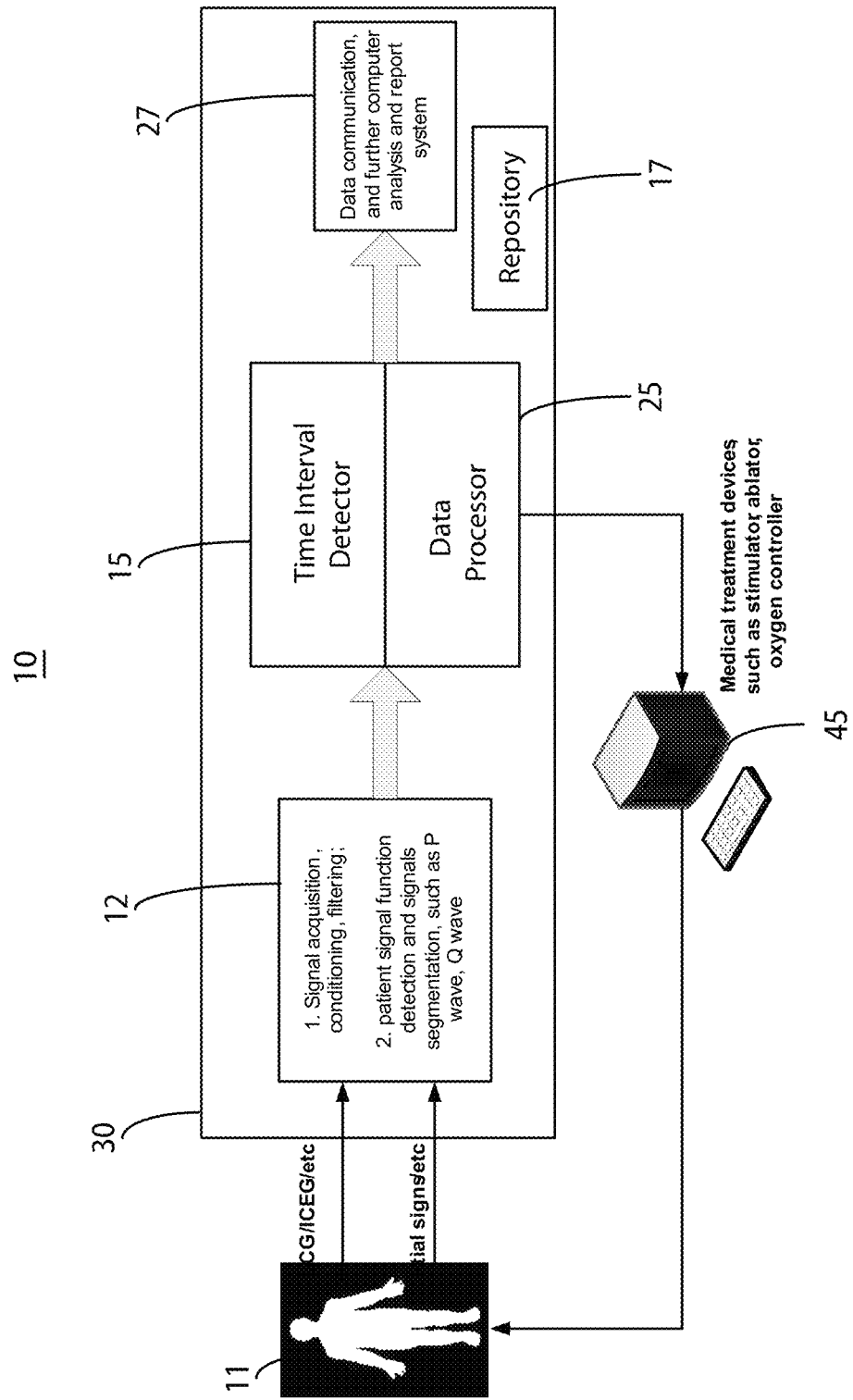
FIG. 1 shows a system for analyzing cardiac electrophysiological signals, according to invention principles.

A system analyzes and characterizes cardiac electrophysiological signals (including surface ECG signals and intra-cardiac electrograms) to identify pathology related signal distortion based on signal portion interval timing and frequency, analysis. The system analyzes and monitors atrial and ventricular signal portion time interval and frequency associated parameters and performs statistical evaluation of these parameters, including variation and variability calculation to determine an accurate time, location and severity of cardiac pathology and events.

Cardiac abnormalities and pathological symptoms are often slowly emerging. Some cardiac arrhythmias are non-symptomatic and usually last a period of time before abnormal electrophysiological signal changes are exhibited (in an ECG and ICEG signal), such as ST segment elevation for more than 0.1 mV indicating ischemia. In addition, different kinds of cardiac diseases may affect different parts of cardiac tissue, such as atrial fibrillation distortion a P wave, myocardial ischemia distortion of an ST segment level. A system analyzes a cardiac electrophysiological signal portion interval, between corresponding cycle points of the same type, that spans multiple sequential heart cycles. The system also analyzes a cardiac electrophysiological signal portion interval, between different cycle points, that spans multiple sequential heart cycles. Thereby the system identifies pathology related signal distortion based on signal portion time interval and frequency, analysis. The system analyzes and monitors atrial and ventricular signal portion interval time and frequency associated parameters and performs statistical evaluation of these parameters, including variation and variability to determine an accurate time, location and severity of cardiac pathology and events. The system detects events occurring between different cardiac chambers, tissues, signal segments, function components and timing phases. In most cardiac arrhythmia cases, pathologies and arrhythmias are exhibited by signal fluctuation and distortion. For example, usually there is a period of time (seconds to hours) with cardiac signal and electrophysiological activity variability before occurrence of a life threatening event. Hence rapid analysis of cardiac signals and response within a limited time portion is desirable for diagnosis and detection.

The system quantitatively identifies cardiac disorders, differentiates cardiac arrhythmias, characterizes pathological severity, predicts life-threatening events, and is usable in evaluating effects of drug administration. The system compares multiple waveform signal portions and performs data analysis for cardiac arrhythmia detection, including between atrial and ventricular response signals, or between different portions of cardiac signals. The system uses electrophysiological energy, excitation and activity of signal portions between atrial chamber and ventricular chamber response waveforms or for intervening tissue portions.

FIG. 1 shows system 10 for analyzing cardiac electrophysiological signals for automatic warning and treatment by analyzing a cardiac trophysiological electrophysiological signal portion interval, between the same or different cycle points, that spans multiple sequential heart cycles. System 10 comprises at least one processing device 30 (such as a computer, server, controller, microprocessor, phone, notebook) for controlling a medical treatment device 45 such as an ablation device or oxygen unit. Device 30 includes acquisition processor 12, time interval detector 15, data processor 25, repository (database) 17 and output processor 27. Different portions of ECG and ICEG signals (such as PT, QT portions) are acquired by at least one processing device 30. Specifically, acquisition processor 12 acquires signal data representing heart electrical activity over multiple heart cycles from patient 11. An individual heart cycle comprises a signal portion between successive sequential R waves. Processor 12 filters, buffers and conditions the acquired signals and detects P, Q, R, S, T, U wave segments of heart cycles and end-of-diastolic (EoD) and end-of-systolic (EoS) points.

The P wave, Q wave, R wave, S wave, T wave, U wave portions and points of the received ECG signal are identified by detecting peaks within the received ECG data using a known peak detector and by segmenting the ECG signal into windows where the waves are expected and by identifying the peaks within the windows. The start point of a wave, for example, is identified by a variety of known different methods. In one method a wave start point comprises where the signal crosses a baseline of the signal (in a predetermined wave window, for example). Alternatively, a wave start point may comprise a peak or valley of signal. The baseline of the signal may comprise a zero voltage line if a static (DC) voltage signal component is filtered out from the signal. The signal processor time interval detector 15 determines time duration between the signal peaks and valleys. The time detector uses a clock counter for counting a clock between the peak and valley points and the counting is initiated and terminated in response to the detected peak and valley characteristics. Time interval detector 15 uses a signal peak detector for detecting multiple successive time intervals including individual time intervals comprising a time interval between a first peak occurring in a first heart cycle and a second peak occurring in at least one of, (a) a successive sequential second heart cycle and (b) a third heart cycle successive and sequential to the second heart cycle.

Data processor 25 processes the multiple detected successive time intervals by, determining at least one interval parameter of, a mean, variance and standard deviation of the time intervals and generates an alert message in response to the interval parameter. Output processor 27 communicates the alert message and associated data to a destination for further processing and recording and storage in repository 17. System 10 facilitates earlier detection and characterization of a cardiac arrhythmia event, severity, location and its timing within a heart cycle. This helps to automatically and adaptively adjust treatment, such as energy, duration, frequency of a stimulator, pacemaker or ablation device.

Figure 2:
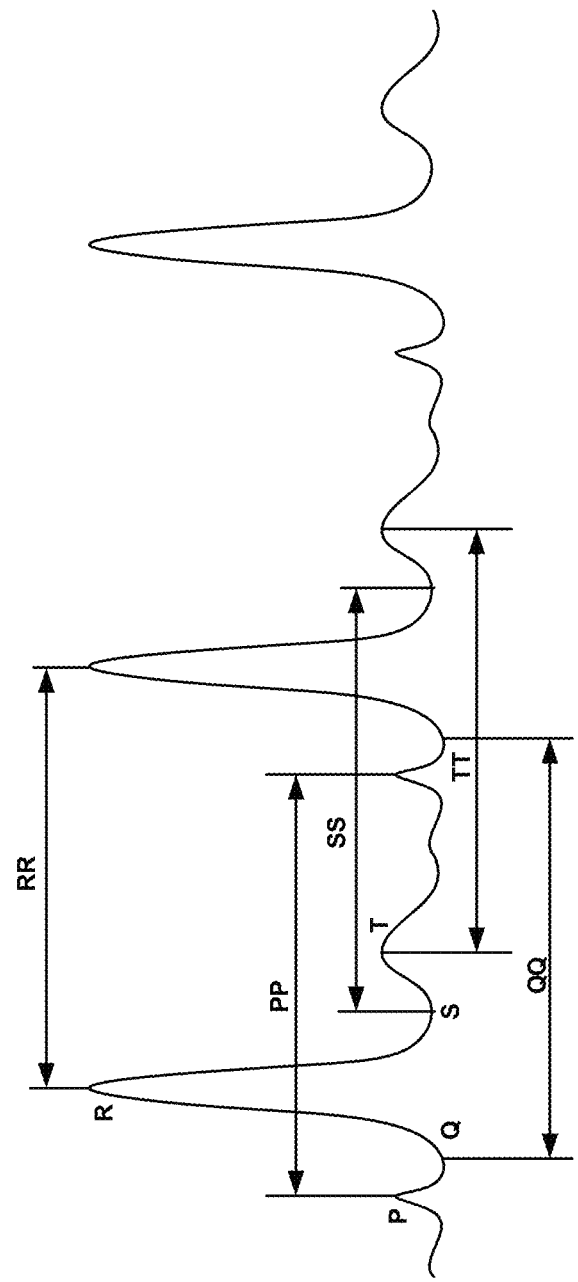
FIG. 2 shows time intervals between a first peak occurring in a first heart cycle and a second peak occurring in a successive sequential different heart cycle, according to invention principles.

FIG. 2 shows time intervals between a first peak occurring in a first heart cycle and a corresponding second peak of the same type occurring in a successive sequential different heart cycle. Parameters determined by system 10 including PP, QQ, RR, SS and TT intervals are shown in three heart cycles of a surface ECG signal. System 10 (FIG. 1) analyzes a cardiac electrophysiological signal portion interval, between corresponding cycle points of the same type, that spans multiple sequential heart cycles which may be within the same time episode or at different time episodes, for the same cardiac function module (such as QRS complex timing), and/or same chamber (atrial or ventricular), and/or segment (such as an ST segment), to determine parameters and detect cardiac impairment. The determined parameters also include calculated statistical parameters including a dispersity parameter and mean, standard deviation and variance parameters. Cardiac electrophysiological excitation (for pacing) is initiated from a right atrial chamber, and conducts to other portions of atrial tissue and reaches a ventricular chamber and tissue. Different portions of tissue exhibit function abnormality in atrial and ventricular chambers and may distort synchronization and cardiac timing between atrial to atrial, ventricular to ventricular, and atrial to ventricular electrophysiological activities. System 10 advantageously derives parameters based on different timing and intervals spanning different numbers of heart cycles for different segments of heart tissue.

FIG. 3 shows a Table identifying statistical parameters indicated in column 306 derived from PP, QQ, RR, SS and TT time intervals identified in column 303 and associated electrophysiological functions described in column 309. A time window for a statistical parameter calculation is adaptively selected by system 10 (or a user) in response to a determined noise level and type of clinical application. Usually a 5-10 heart beat window is selected. In column 306 mean(●) represents the mean or average value of the parameter in a selected window; Var(●) is calculated using, $$\sum_{x_i \in selected\_time\_window} (x_i - \text{mean}(x_i))^2,$$

where $x_i$ is the data series of the value inside a time window; standard deviation is the square root of Var(●). A dispersity parameter comprises a ratio between maximum value of the data series in the time window and standard deviation. A variation parameter comprises a ratio between a mean value mean(●) and variance Var(●). In other embodiments other time intervals are used such as between U waves or between onset of P waves, over multiple heart cycles, for example, in order to detect cardiac function changes and variation. The FIG. 3 parameters are used in cardiac function tracking of the same portion of cardiac tissue, such as a region of a heart chamber to determine change from heart cycle to heart cycle. However, the parameters may not be able to track electrophysiological signal conduction variation and changes within a single heart cycle.

FIG. 4 shows time intervals between a first peak of a first ECG wave type occurring in a first heart cycle and a second peak of a different second ECG wave type occurring in a successive sequential different heart cycle. The time intervals are from an atrial P wave to other electrophysiological signal waveform points. Parameters determined by system 10, including PQ, PR, PS, PT and PU intervals are shown in three heart cycles of a surface ECG signal. In other embodiments, additional different intervals are analyzed including, QR, QT, QU and SU intervals and from onset of atrial depolarization to onset of ventricular repolarization. System 10 (FIG. 1) analyzes a cardiac electrophysiological signal portion interval, between different types of heart cycle points, that spans multiple sequential heart cycles. The time intervals analyzed may be within the same time episode or different time episodes, for the same cardiac function module (such as QRS complex timing), and/or same chamber (atrial or ventricular), to determine parameters and detect cardiac impairment. The system identifies pathology related signal distortion based on signal portion time interval and frequency, analysis. System 10 advantageously uses time intervals between different points of different ECG heart cycles to track timing variation, function and conduction transitions, and chamber activity by comparing different time intervals.

System 10 adaptively selects parameters for calculation in response to type of pathology to be detected, e.g. arrhythmia, myocardial infarction. The calculated parameters that may be calculated include the following.
Averaging timing interval value: mean($T_{PS}$)
Time interval variance parameter: Var($T_{PS}$)
Time interval standard deviation parameter: STD($T_{PS}$)
Time interval dispersity parameter: MAX ($T_{PS}$)/STD($T_{PS}$)
Time interval variation parameter: mean($T_{PS}$)/Var($T_{PS}$)
In response to a user determined diagnostic function being performed, parameters are used for multiple interval type adaptive analysis as follows.
Multiple interval type average parameter:

$$\text{Mean}(multi) = \sum_{i \in ROI\_heart\_signal} \text{mean}(T_i)$$

Multiple interval type variance parameter:

$$\text{Var}(multi) = \sum_{i \in ROI\_heart\_signal} \text{Var}(T_i)$$

Multiple interval standard deviation parameter:

$$\text{STD}(multi) = \sum_{i \in ROI\_heart\_signal} \text{STD}(T_i)$$

Multiple interval type dispersity parameter:

$$\text{Dispersity}(multi) = \sum_{i \in ROI\_heart\_signal} \frac{\text{MAX}(T_i)}{\text{STD}(T_i)}$$

Multiple interval type variation parameter:

$$\text{Variation}(multi) = \sum_{i \in ROI\_heart\_signal} \frac{\text{mean}(T_i)}{\text{Var}(T_i)}$$

System 10 uses different statistical analyses, such as t test and sequential probability test to improve sensitivity and reliability of time interval based cardiac arrhythmia detection. In other embodiments, other parameters are used for heart function analysis and comparison, including frequency spectrum and energy pattern analysis.

Figure 5:
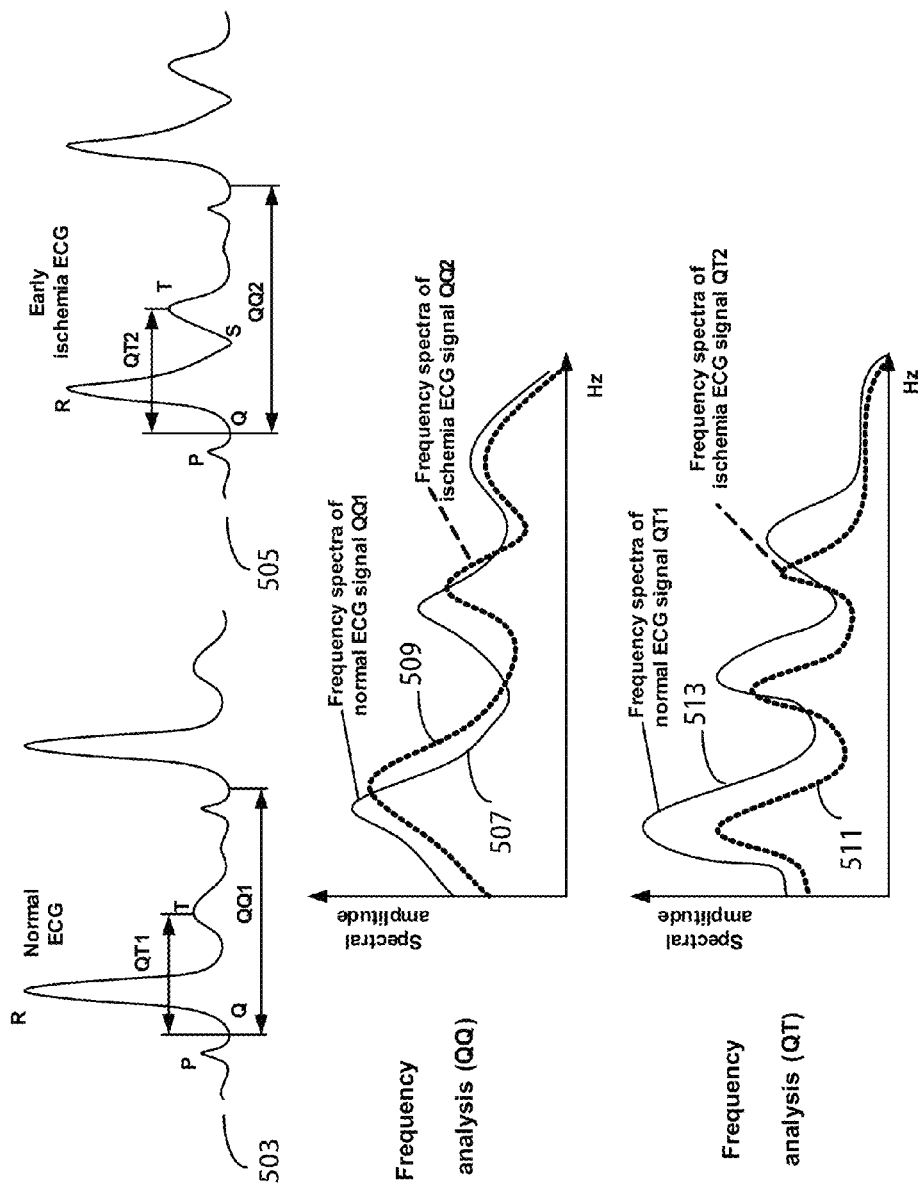
FIG. 5 illustrates frequency spectral analysis of time intervals between a first peak occurring in a first heart cycle and a second peak occurring in a successive sequential different heart cycle, according to invention principles.

FIG. 5 illustrates frequency spectral analysis of time intervals between a first peak occurring in a first heart cycle and a second peak occurring in a successive sequential different heart cycle. System 10 (FIG. 1) detects and characterizes small changes (usually morphology changes in the time domain waveform are small, especially in an early stage of a heart condition) by using calculated time interval frequency spectral energy parameters. ECG signal portion waveform 503 shows a normal healthy heart beat cycle and ECG signal portion waveform 505 shows an early ischemia heart cycle. Waveforms 503 and 505 indicate QQ and QT signal portions selected for ventricle chamber based pathology diagnosis using frequency and energy analysis. System 10 derives frequency spectra distribution curves 507, 509 comprising normalized amplitude versus frequency (Hz) for the QQ time interval signal portion for the normal and ischemia signals, respectively. System 10 also derives frequency spectra distribution curves 511, 513 comprising normalized amplitude versus frequency (Hz) for the QT time interval signal portion for the normal and ischemia signals, respectively.

System 10 analyzes different signal portions in an ECG signal by determining frequency and energy data associated with the portions. A physician or a patient monitoring device adaptively selects a portion (such as a PT, PR portion, for example) of an ECG signal in response to type of clinical application (such as a ventricular diagnosis). In the simulation of FIG. 5, QQ and QT portions are selected for ventricular function detection and characterization using frequency spectral analysis. The frequency and energy parameters are defined as follows.

Unilateral_energy_sync$_{signal\_portion}$ =

$$\frac{\int_{x \in ROI\_bandwidth\_of\_the\_unilateral\_signal} |f(x)|^2_{monitoring\_signal\_portion}}{\int_{x \in ROI\_bandwidth\_of\_the\_unilateral\_signal} |f(x)|^2_{healthy\_signal\_portion}}$$

Bilateral_energy_sync$_{signal\_portion}$ =

$$\frac{\int_{x \in ROI\_bandwidth\_of\_the\_bilateral\_signal} |f(x)|^2_{monitoring\_signal\_portion}}{\int_{x \in ROI\_bandwidth\_of\_the\_bilateral\_signal} |f(x)|^2_{healthy\_signal\_portion}}$$

Where, unilateral concerns a signal portion interval between the same type of cycle points of different heart cycles, bilateral concerns a signal portion interval between different types of cycle points of different heart cycles. Further, signal_portion is a signal of interest portion selected for cardiac function analysis, such as atrial chamber, ventricular tissue. ROI_bandwidth_of_the_unilateral_signal and ROI_bandwidth_of_the_bilateral_signal concern the ROI interest signal portion for unilateral or bilateral signal analysis; the bandwidth is selected, e.g. from 10-100 Hz, 50-300 Hz, determined by the system in response to clinical application (such as time interval frequency range) and noise level and noise bandwidth, f(x) is the frequency spectral function (amplitude) of the ROI selected signals. Calculated frequency and energy parameters are used to detect and characterize pathology related changes in cardiac data and signals.

Figure 6:
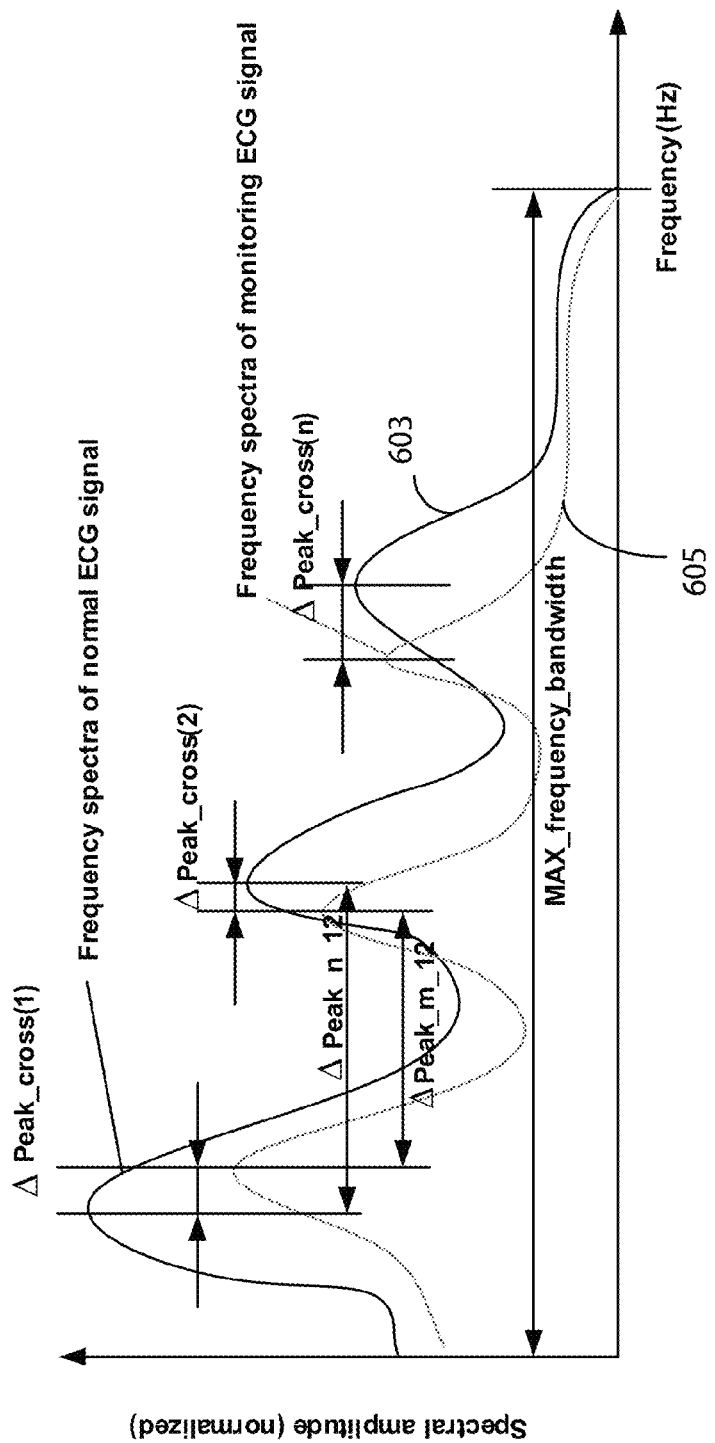
FIG. 6 shows healthy and pathological spectral frequency distributions of a portion of an ECG signal showing frequency peak variation used to detect pathology, according to invention principles.

FIG. 6 shows healthy and pathological spectral frequency distributions of a portion of an ECG signal showing frequency peak variation used to detect pathology. System 10 derives frequency spectra distribution curves 603, 605 comprising normalized amplitude versus frequency (Hz) for a signal portion for normal and pathological signals, respectively. The frequency distribution of the two episodes show peak variation and latency differences used to detect and characterize signal variation indicating a pathological heart beat. In FIG. 6, $\Delta$Peak_n_12 represents a frequency distance between a first peak and second peak in a normal heart ECG signal 603 while $\Delta$Peak_m_12 represents a frequency distance between a first peak and second peak in a monitoring heart signal (acquired or previously stored signal compared with a corresponding same frequency peaks; $\Delta$Peak_cross normal signal).

System 10 determines an interval between (n) represents a frequency interval (Hz) between an $n^{th}$ peak of a normal signal and an $n^{th}$ peak of a pathological or monitored signal; MAX_frequency_bandwidth is a frequency maximum range of an analyzed signal portion; a cutoff frequency of a MAX_frequency_bandwidth is adaptively adjusted in response to clinical application (or user command) and is not necessarily a true signal maximum frequency bandwidth.

Frequency interval parameters are determined for Unilateral and Bilateral frequency peak intervals:

$$\text{mutual\_frequency\_sync}_{unilateral\_ij} = \frac{\text{mean}(\Delta\text{peak\_m\_ij})}{\text{STD}(\Delta\text{peak\_m\_ij})} \bigg|(t)$$

$$\text{mutual\_frequency\_sync}_{bilateral\_ij\_pq} = \frac{\text{mean}(\Delta\text{peak\_m\_ij})}{\text{mean}(\Delta\text{peak\_m\_pq})} \bigg|(t)$$

Where mutual_frequency_sync$_{unilateral\_ij}$ comprises variation in a frequency interval between a #i peak to #j peak while mutual_frequency_sync$_{bilateral\_ij\_pq}$ represents a bilateral mutual frequency interval parameter comprising a ratio between two kinds of peak distance: mean($\Delta$peak_m_ij) vs. mean($\Delta$peak_m_pq); mean($\Delta$peak_m_ij) represents an average value of an interval between frequency peaks in a frequency distribution between #i peak to #j peak; STD($\Delta$peak_m_ij) represents a standard deviation parameter of an interval between frequency peaks in a frequency distribution between #i peak to #j peak; symbol |(t) represents a time stamp associated with a calculation used in real time signal portion monitoring. Typically there are 3-4 peaks in a portion of interest of a signal frequency distribution, so peaks 1-3 are typically used for cardiac pathology detection, such as mutual_frequency_sync$_{unilateral\_12}$ and mutual_frequency_sync$_{bilateral\_12\_23}$. System 10 derives a frequency parameter using different frequency distributions of different kinds of signal frequency functions. A cross frequency parameter is used to evaluate signal variation due to the cardiac arrhythmias.

$$\text{Cross\_mutual\_frequency\_sync} = \frac{\sum_{i \in \text{ROI\_frequency\_bandwidth}} \Delta\text{peak\_cross}(i)}{\text{MAX\_frequency\_bandwidth}} \bigg|(t)$$

Or $$\text{Cross\_mutual\_frequency\_sync}_{ij} = \frac{|\Delta\text{peak\_cross}(i) - \Delta\text{peak\_cross}(j)|}{\text{MAX\_frequency\_bandwidth}} \bigg|(t)$$

Where Cross_mutual_frequency_sync$_{ij}$ is a cross peak deviation summation for frequency deviation of corresponding peaks in a frequency distribution; MAX_frequency_bandwidth is a signal portion frequency bandwidth. One type of cross mutual frequency calculation comprises a cross peak deviation where a bigger value indicates more severity of cardiac abnormality. Another type of cross mutual frequency calculation comprises frequency deviation between two different types of frequency peaks in frequency distributions representing a first normal (healthy) signal and a current monitoring signal. The system may be implemented in hardware in a vital sign signal monitoring and treatment device, such as an ICD (intra-cardiac device), ablator, vital sign monitor-calculator.

Figure 7:
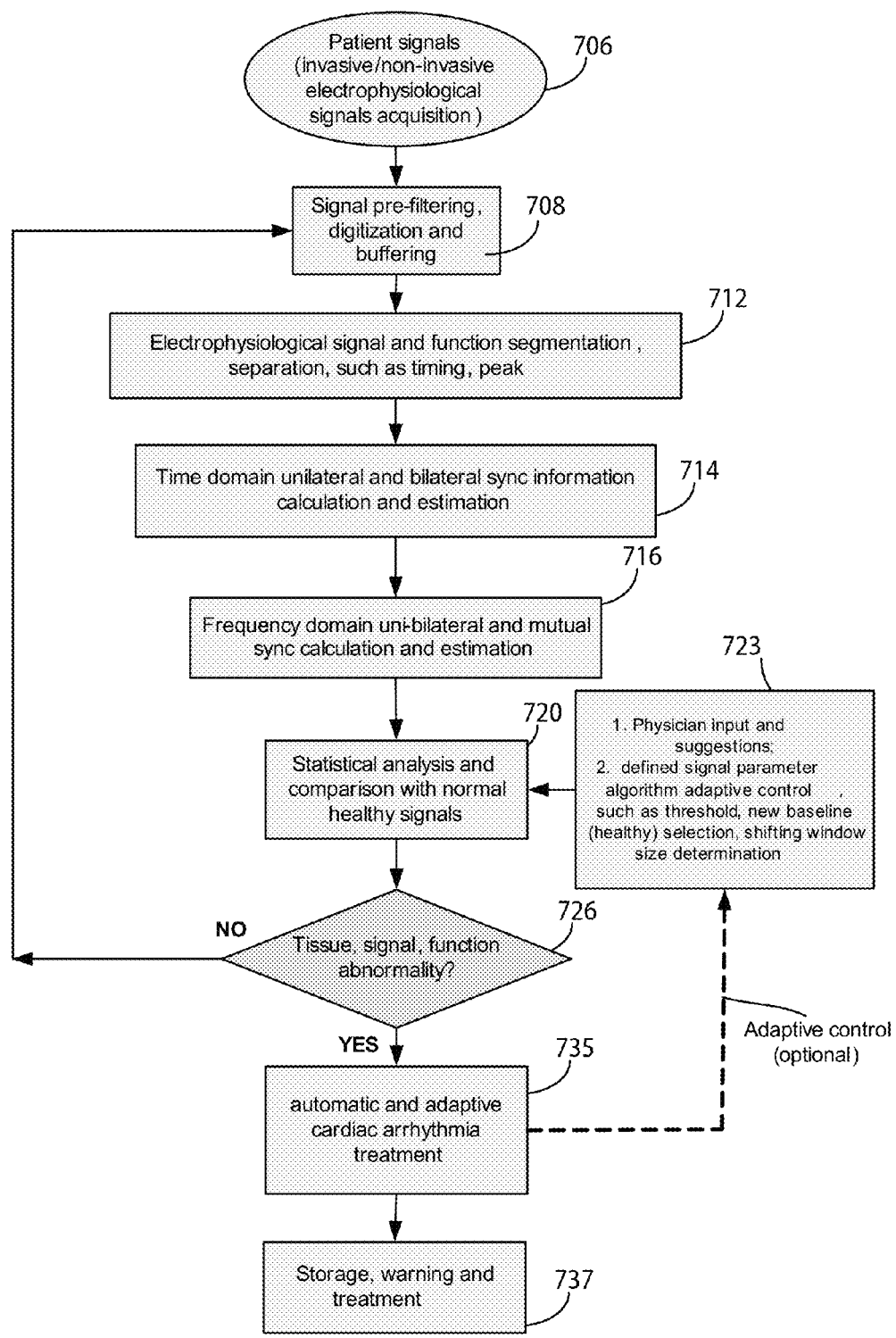
FIG. 7 shows a flowchart of a method for patient electrophysiological parameter calculation and cardiac arrhythmia detection and characterization, according to invention principles.

FIG. 7 shows a flowchart of a method used by system 10 (FIG. 1) for patient electrophysiological parameter calculation and cardiac arrhythmia detection and characterization using heart electrical activity signal time and frequency interval analysis. Acquisition processor 12 in step 706 acquires invasive and non-invasive signal data representing heart electrical activity over multiple heart cycles. An individual heart cycle comprises a signal portion between successive sequential R waves. In step 708 processor 12 buffers, filters (to remove power line noise, patient movement and respiration noise) and digitizes an ECG signal and ICEG signal, acquired in step 706. Detector 15 in step 708 filters the received signal data using a filter adaptively selected in response to data indicating clinical application, to remove patient movement and respiratory artifacts as well as power line noise. In step 712, time interval detector 15 detects patient signal parameters and segments an ECG signal into sections including, P wave, Q wave, R wave, S wave, T wave and U wave portions and determines peak timing and end-of-diastolic (EoD) and end-of-systolic (EoS) points. Detector 15 also detects ECG signal amplitude peaks and data processor 25 detects peaks in a frequency waveform derived from an ECG signal. Specifically, detector 15 uses a signal peak detector for detecting multiple successive time intervals including individual time intervals comprising a time interval between a first peak occurring in a first heart cycle and a second peak occurring in at least one of, (a) a successive sequential second heart cycle and (b) a third heart cycle successive and sequential to the second heart cycle. The first and second peaks comprise the same type of ECG signal peak (unilateral analysis) or a different type of ECG signal peak (bilateral analysis). Data processor 25 detects peaks in a frequency waveform derived from an ECG signal and determines and compares frequency component spectral peaks of corresponding frequency components of the signal data in different individual time intervals of the multiple detected successive time intervals.

In step 714, data processor 25 processes the multiple detected successive time intervals by, determining at least one interval parameter comprising, a mean, variance and standard deviation of the time intervals and parameters of the Table of FIG. 3 and other parameters previously described. In step 716, data processor 25 processes the multiple detected successive time intervals by determining and comparing frequency component spectral peaks of corresponding frequency components of the acquired signal data in different individual time intervals of the multiple detected successive time intervals. Processor 25 determines the frequency, spectral and energy parameters previously described in connection with FIGS. 5 and 6. Parameters determined are selected in response to a clinical application or procedure being performed, such as QT interval related parameters for ventricular chamber analysis, PR interval related parameters for atrial chamber analysis. In step 720, processor 25 performs the statistical analysis as previously described, on the parameters determined in step 716.

In step 726, if processor 25 determines that no cardiac function or tissue abnormality is detected, the process is repeated from step 708. If processor 25 determines that cardiac function or tissue abnormality is detected, processor 25 in step 735 performs adaptive cardiac arrhythmia treatment of a patient. In step 737 output processor 27 stores data representing the calculated parameters, treatment used and generated warning in repository 17. Processor 25 in step 723 adaptively adjusts thresholds, baseline signal levels and window used for sample selection for processing.

Figure 8:
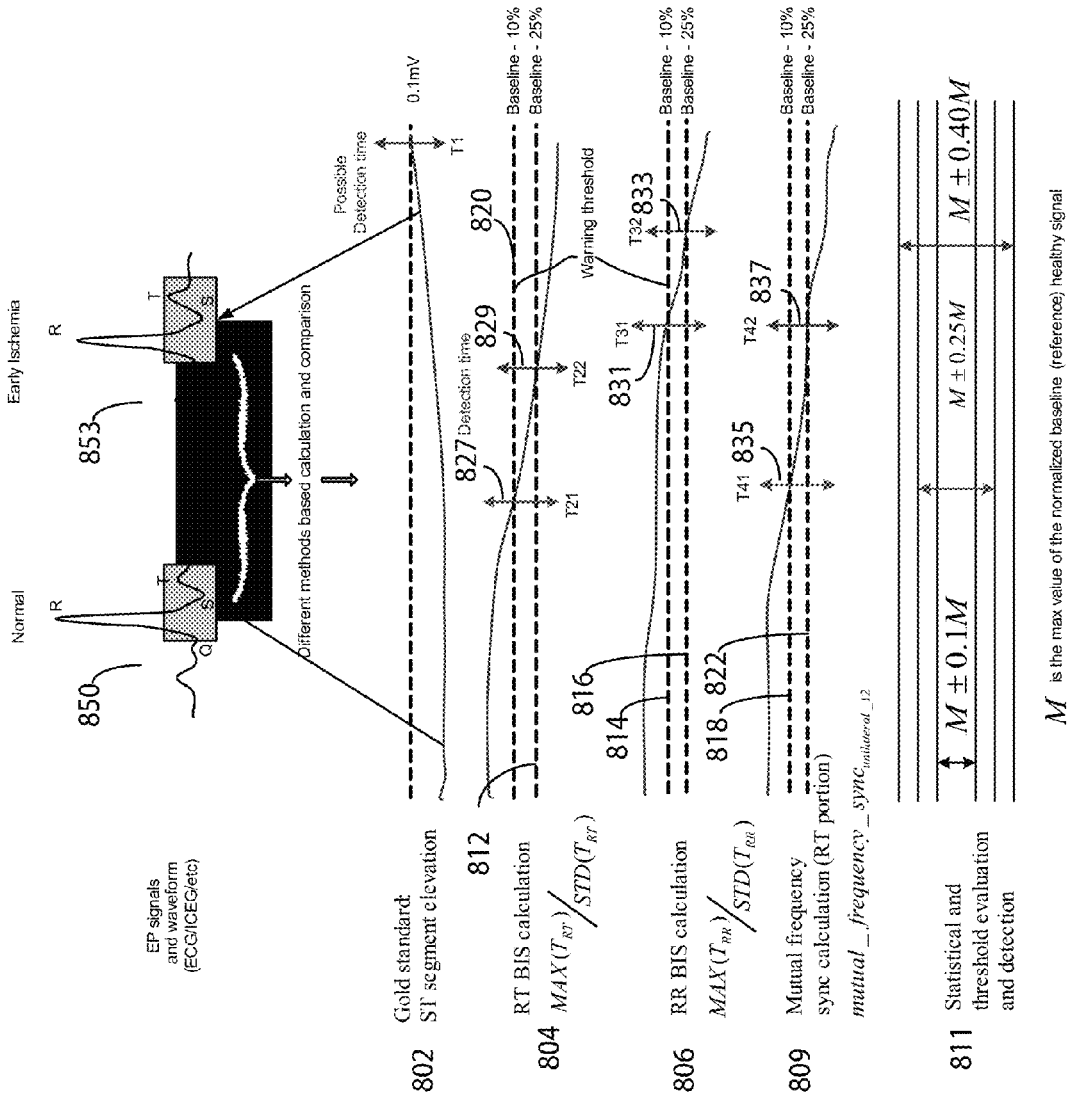
FIG. 8 illustrates myocardial infarction detection, according to invention principles.

FIG. 8 illustrates myocardial infarction detection by system 10 (FIG. 1) in an ischemia event simulation data analysis in a left ventricle. A single channel surface ECG signal shows a myocardial infarction simulation involving normal 850 and myocardial infarction 853 stages. Different calculated parameters are compared, including standard 0.1 mV elevation of an ST segment 802, an RT time interval dispersity parameter: $MAX(T_{RT})/STD(T_{RT})$ 804, an RR time interval dispersity parameter: $MAX(T_{RR})/STD(T_{RR})$ 806 and variation in a frequency interval between peak 1 to 2

$$\text{mutual\_frequency\_sync}_{unilateral\_ij} = \frac{\text{mean}(\Delta\text{peak\_m\_ij})}{STD(\Delta\text{peak\_m\_ij})}\bigg|(t). \qquad 809$$

Data processor 25 (FIG. 1) uses predetermined baseline −10% (814, 818, 820) and −25% thresholds (812, 816, 822) to identify and characterize ECG signal changes for normal and high probability warning of myocardial ischemia event detection. The thresholds are also used for ischemia event severity level analysis. A 10-heart-beat window size is used for averaging to obtain a mean and standard deviation value for a calculated parameter, such as the timing and frequency parameters previously described, for example. Normal signals are used as a reference and baseline in the calculation. Arrows 827, 831, 835 show the detection time point corresponding to the 10% threshold and Arrows 829, 833, 837 show the detection time point corresponding to the 25% threshold (the threshold is adaptively dynamically changed by system 10).

The calculated parameters are used for analysis of different parts of cardiac tissue and cardiac functions and different kinds of cardiac arrhythmia detection, diagnosis and characterization, such as for atrial fibrillation and ventricular tachycardia. A calculation method is selected and determined by a user or automatically by the system in response to data identifying clinical application and factors such as sensitivity ratio, reliability of calculation, window size used for averaging, calculation time step and warning threshold. If different leads and channel signals are used in a calculation and evaluation, the severity, location, timing, and level of needed treatment, of myocardial ischemia are captured and characterized.

As shown, ST segment elevation detects myocardial ischemia at T1=100 seconds. The RT time interval dispersity parameter calculation detects myocardial ischemia with two levels: normal (827) T21=50 seconds with high confidence (829) T22=75 seconds. The RR time interval dispersity parameter calculation detects the ischemia event with two levels: normal (831) T21=79 seconds with high confidence (833) T22=91 seconds. The variation in frequency interval between peak 1 to 2 calculation (using RT portions signal for the spectral distribution since the example is for ventricular ischemia detection) detects the ischemia event at (835) T41=52 seconds and (837) T42=77 seconds. The RT time interval and RT frequency interval calculations provide improved (earlier and more reliable) ischemia event detection since myocardial ischemia mostly affects repolarization of ventricular portion signals, which is the RT portion. Selectable thresholds 811 are also shown. The parameter calculations are used for identifying cardiac disorders, differentiating cardiac arrhythmias, characterizing pathological severity, predicting life-threatening events, and initiating heart medical treatment, such as drug delivery and long term cardiac care (and may be used in a bedside cardiac monitoring system or portable patient cardiac function monitoring and analysis system, such as Holter Monitoring and ICD (Intra-cardiac devices).

Figure 9:
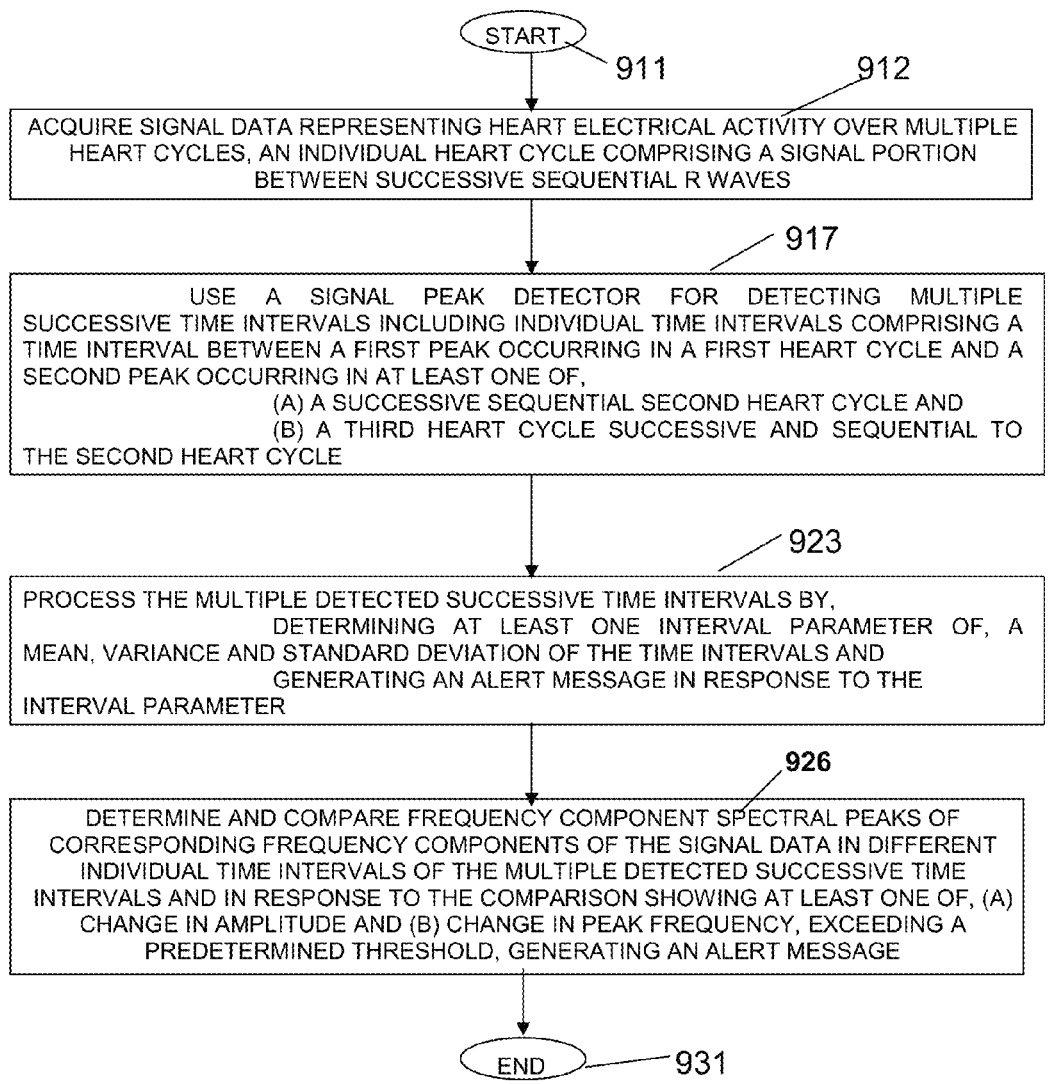
FIG. 9 shows a flowchart of a process used for analyzing cardiac electrophysiological signals, according to invention principles.

FIG. 9 shows a flowchart of a process used by system 10 (FIG. 1) for analyzing cardiac electrophysiological signals. In step 912 following the start at step 911, acquisition processor 12 acquires signal data representing heart electrical activity over multiple heart cycles. An individual heart cycle comprises a signal portion between successive sequential R waves, for example. In step 917, time interval detector 15 uses a signal peak detector for detecting multiple successive time intervals including individual time intervals comprising a time interval between a first peak occurring in a first heart cycle and a second peak occurring in at least one of, (a) a successive sequential second heart cycle and (b) a third heart cycle successive and sequential to the second heart cycle. In bilateral embodiments, the first peak comprises a P wave and the second peak comprises at least one of, a Q wave, S wave, T wave and U wave. In a further embodiment, the first peak comprises an S wave and the second peak comprises a T wave. In different unilateral embodiments, the first and second peaks both comprise a P wave, the first and second peaks both comprise a Q wave, the first and second peaks both comprise an R wave, the first and second peaks both comprise an S wave, or the first and second peaks both comprise a T wave, for example.

Data processor 25 in step 923 processes the multiple detected successive time intervals by, determining at least one interval parameter of, a mean, variance and standard deviation of the time intervals and by generating an alert message in response to the interval parameter. Data processor 25 uses predetermined mapping information, associating ranges of the interval parameter or a value derived from the interval parameter with corresponding medical conditions, and compares the interval parameter or the value derived from the interval parameter, with the ranges and generates an alert message indicating a potential medical condition. The predetermined mapping information associates ranges of the interval parameter or a value derived from the interval parameter with particular patient demographic characteristics and with corresponding medical conditions and the data processor uses patient demographic data including at least one of, age weight, gender and height in comparing the interval parameter or a value derived from the interval parameter with the ranges and generating an alert message indicating a potential medical condition. Data processor 25 uses predetermined mapping information, associating thresholds of the interval parameter or a value derived from the interval parameter with corresponding medical conditions, and compares the interval parameter or the value derived from the interval parameter, with the thresholds and generates an alert message indicating a potential medical condition.

In step 926, processor 25 determines and compares frequency component spectral peaks of corresponding frequency components of the signal data in different individual time intervals of the multiple detected successive time intervals and in response to the comparison showing at least one of, (a) change in amplitude and (b) change in peak frequency, exceeding a predetermined threshold, generates an alert message. Data processor 25 determines and compares peak frequency component energy representative values of corresponding frequency components of the signal data in different individual time intervals of the multiple detected successive time intervals and in response to the comparison showing change in peak frequency component energy representative value exceeding a predetermined threshold, generates an alert message. The energy representative value of a frequency component peak is derived in response to an integral of the square of frequency component amplitude values of the frequency component peak.

Processor 25 in one embodiment, determines and compares frequency component spectral peak amplitude of corresponding frequency components of the signal data in different individual time intervals of the multiple detected successive time intervals by comparing at least one of mean, variance and standard deviation of peak frequency component amplitude of the signal data in the different individual time intervals. Processor 25 determines and compares frequency component spectral peaks of corresponding frequency components of the signal data in different individual time intervals of the multiple detected successive time intervals by comparing at least one of mean, variance and standard deviation of peak frequency of the signal data in the different individual time intervals. Processor 25 uses predetermined mapping information, associating ranges of frequency component spectral peak amplitude or a value derived from the frequency component spectral peak amplitude with corresponding medical conditions, and compares the frequency component spectral peak amplitude or a value derived from the frequency component spectral peak amplitude, with the ranges and generates an alert message indicating a potential medical condition. Further, processor 25 uses predetermined mapping information, associating ranges of frequency component spectral peak frequency or a value derived from the frequency component spectral peak frequency with corresponding medical conditions, and compares the frequency component spectral peak amplitude or a value derived from the frequency component spectral peak frequency, with the ranges and generates an alert message indicating a potential medical condition. The process of FIG. 9 terminates at step 931.

Figure 10:
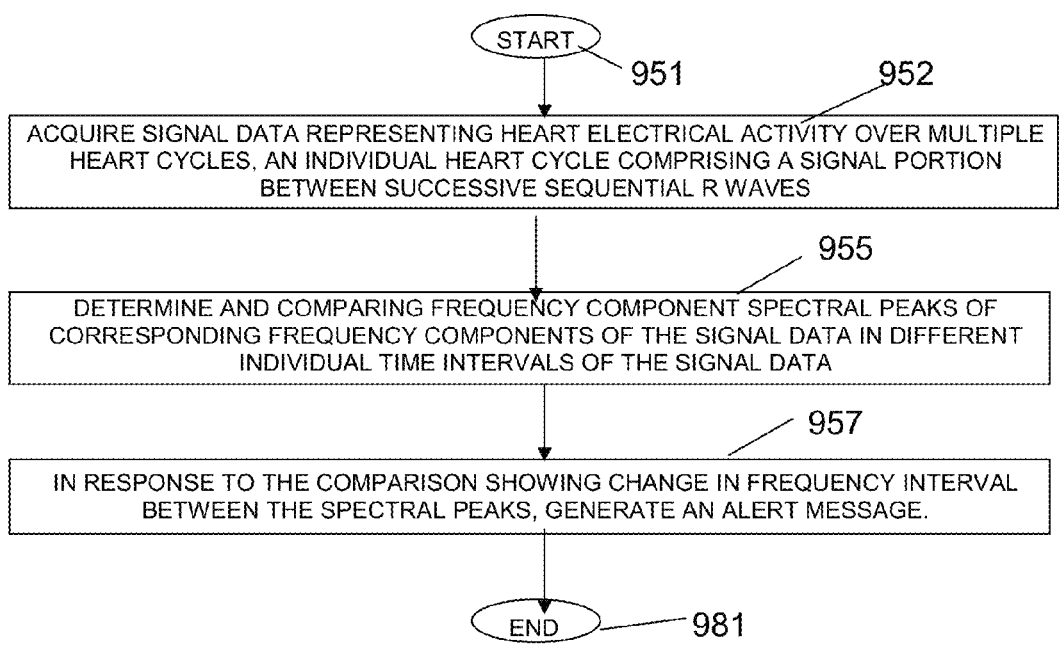
FIG. 10 shows a flowchart of a process used for frequency analysis of cardiac electrophysiological signals, according to invention principles.

FIG. 10 shows a flowchart of a process used for frequency analysis of cardiac electrophysiological signals. In step 952 following the start at step 951, acquisition processor 12 acquires signal data representing heart electrical activity over multiple heart cycles. An individual heart cycle comprises a signal portion between successive sequential R waves, for example. In step 955, data processor 25 processes the signal data by, determining and comparing frequency component spectral peaks of corresponding frequency components of the signal data in different individual time intervals of the signal data. In step 957, in response to the comparison showing change in frequency interval between the spectral peaks, processor 25 generates an alert message. The process of FIG. 10 terminates at step 981.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a computer, controller or microprocessor, for example, and is conditioned using executable instructions to perform special purpose functions not performed by a general purpose computer. A processor may be coupled (electrically and/or as comprising executable components) with any other processor enabling interaction and/or communication therebetween. Computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s). A user interface processor or generator is a known element comprising electronic circuitry or software or a combination of both for generating display elements or portions thereof. A user interface comprises one or more display elements enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display elements, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the elements for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display elements in response to signals received from the input devices. In this way, the user interacts with the display elements using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 1-10 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system analyzes and characterizes cardiac electrophysiological signals (including surface ECG signals and intra-cardiac electrograms) to identify pathology related signal distortion based on signal portion interval timing and frequency related parameter calculation and associated statistical analysis. Further, the processes and applications may, in alternative embodiments, be located on one or more (e.g., distributed) processing devices on a network linking the units FIG. 1. Any of the functions and steps provided in FIGS. 1-10 may be implemented in hardware, software or a combination of both. No claim element herein is to be construed under the provisions of 35 U.S.C. 112, sixth paragraph, unless the element is expressly recited using the phrase "means for."

What is claimed is:

1. A system for analyzing cardiac electrophysiological signals, the system comprising:
   an acquisition processor for acquiring signal data representing heart electrical activity over a plurality of heart cycles, an individual heart cycle comprising a signal portion between successive sequential R waves;
   a time interval detector using a signal peak detector for detecting a plurality of successive time intervals including individual time intervals comprising a time interval from a first peak of a first wave type occurring in a first heart cycle to a second peak of a second different wave type occurring in at least one of,
      (a) a successive sequential second heart cycle and
      (b) a third heart cycle successive and sequential to said second heart cycle; and
   a data processor for processing the plurality of detected successive time intervals by, determining at least one interval parameter of, a mean, variance and standard deviation of said time intervals and generating an alert message in response to said interval parameter.

2. The system of claim 1, wherein said first peak comprises a P wave.

3. The system of claim 2, wherein said second peak comprises at least one of a, Q wave, S wave, T wave and U wave.

4. The system of claim 1, wherein the first peak comprises an S wave and the second peak comprises a T wave.

5. The system of claim 1, wherein said data processor uses predetermined mapping information, associating ranges of said interval parameter or a value derived from said interval parameter with corresponding medical conditions, and compares said interval parameter or said value derived from said interval parameter, with said ranges and generates an alert message indicating a potential medical condition.

6. A system according to claim 5, wherein said predetermined mapping information associates ranges of said interval parameter or a value derived from said interval parameter with particular patient demographic characteristics and with corresponding medical conditions and said data processor uses patient demographic data including at least one of, age, weight, gender and height in comparing said interval parameter or a value derived from said interval parameter with said ranges and generating an alert message indicating a potential medical condition.

7. The system of claim 1, wherein said data processor uses predetermined mapping information, associating thresholds of said interval parameter or a value derived from said interval parameter with corresponding medical conditions, and compares said interval parameter or said value derived from said interval parameter, with said thresholds and generates an alert message indicating a potential medical condition.

8. A system for analyzing cardiac electrophysiological signals, the system comprising:
   an acquisition processor for acquiring normal and monitoring signal data representing heart electrical activity over a plurality of heart cycles, an individual heart cycle comprising a signal portion between successive sequential R waves; and
   a data processor for processing said signal data by,
      determining first frequency spectral distribution for the normal signal data and second frequency spectral distribution for the monitoring signal data,
      determining a frequency interval between corresponding frequency component spectral peaks of the first and second frequency spectral distributions of said normal and monitoring signal data in different individual time intervals of said normal and monitoring signal data, and
      in response to a change in the frequency interval between said spectral peaks, generating an alert message.

9. A system for analyzing cardiac electrophysiological signals, the system comprising:
   an acquisition processor for acquiring normal and monitoring signal data representing heart electrical activity over a plurality of heart cycles, an individual heart cycle comprising a signal portion between successive sequential R waves;
   a time interval detector using a signal peak detector for detecting a plurality of successive time intervals including individual time intervals comprising a time interval from a first peak occurring in a first heart cycle to a second peak occurring in at least one of,
      (a) a successive sequential second heart cycle and
      (b) a third heart cycle successive and sequential to said second heart cycle; and
   a data processor for processing the plurality of detected successive time intervals by,
      determining first frequency spectral distribution for the normal signal data and second frequency spectral distribution for the monitoring signal data,
      comparing frequency component spectral peaks of the first and second frequency spectral distributions of said normal and monitoring signal data in different individual time intervals of said plurality of detected successive time intervals, and
      in response to the comparison showing at least one of,
         (a) change in amplitude and
         (b) change in frequency interval between said spectral peaks, exceeding a predetermined threshold, generating an alert message.

10. The system of claim 9, wherein said data processor determines and compares peak frequency component energy representative values of corresponding frequency components of said normal and monitoring signal data in different individual time intervals of said plurality of detected successive time intervals and in response to the comparison showing change in peak frequency component energy representative value exceeding a predetermined threshold, generates an alert message.

11. The system of claim 10, wherein said energy representative value of a frequency component peak is derived in response to an integral of the square of frequency component amplitude values of said frequency component peak.

12. The system of claim 9, wherein said data processor determines and compares frequency component spectral peak amplitude of corresponding frequency components of said normal and monitoring signal data in different individual time intervals of said plurality of detected successive time intervals by comparing at least one of mean, variance and standard deviation of peak frequency component amplitude of said normal and monitoring signal data in said different individual time intervals.

13. The system of claim 9, wherein said data processor determines and compares frequency component spectral peaks of corresponding frequency components of said normal and monitoring signal data in different individual time intervals of said plurality of detected successive time intervals by comparing at least one of mean, variance and standard deviation of peak frequency of said normal and monitoring signal data in said different individual time intervals.

14. The system of claim 9, wherein said data processor uses predetermined mapping information, associating ranges of frequency component spectral peak amplitude or a value derived from said frequency component spectral peak amplitude with corresponding medical conditions, and compares said frequency component spectral peak amplitude or a value derived from said frequency component spectral peak amplitude, with said ranges and generates an alert message indicating a potential medical condition.

15. The system of claim 9, wherein said data processor uses predetermined mapping information, associating ranges of frequency component spectral peak frequency or a value derived from said frequency component spectral peak frequency with corresponding medical conditions, and compares said frequency component spectral peak amplitude or a value derived from said frequency component spectral peak frequency, with said ranges and generates an alert message indicating a potential medical condition.

16. A method for analyzing cardiac electrophysiological signals, comprising the activities of:
    acquiring signal data representing heart electrical activity over a plurality of heart cycles, an individual heart cycle comprising a signal portion between successive sequential R waves;
    using a signal peak detector for detecting a plurality of successive time intervals including individual time intervals comprising a time interval from a first peak of a first wave type occurring in a first heart cycle to a second peak of a second different wave type occurring in at least one of,
        (a) a successive sequential second heart cycle and
        (b) a third heart cycle successive and sequential to said second heart cycle; and
    processing the plurality of detected successive time intervals by, determining at least one interval parameter of, a mean, variance and standard deviation of said time intervals and generating an alert message in response to said interval parameter.

17. The method of claim 16, wherein said first peak comprises a P wave.

18. The method of claim 17, wherein said second peak comprises at least one of a, Q wave, S wave, T wave and U wave.

\* \* \* \* \*